(12) United States Patent
Kanemaru

(10) Patent No.: US 10,646,175 B2
(45) Date of Patent: May 12, 2020

(54) X-RAY COMPUTED TOMOGRAPHY APPARATUS

(71) Applicant: Canon Medical Systems Corporation, Otawara-shi (JP)

(72) Inventor: Takashi Kanemaru, Yaita (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 16/122,377

(22) Filed: Sep. 5, 2018

(65) Prior Publication Data

US 2019/0069857 A1   Mar. 7, 2019

(30) Foreign Application Priority Data

Sep. 5, 2017   (JP) .................... 2017-170461

(51) Int. Cl.
*A61B 6/00*   (2006.01)
*A61B 6/03*   (2006.01)

(52) U.S. Cl.
CPC .......... *A61B 6/4021* (2013.01); *A61B 6/032* (2013.01); *A61B 6/405* (2013.01); *A61B 6/4266* (2013.01); *A61B 6/461* (2013.01)

(58) Field of Classification Search
CPC ..... A61B 6/4021; A61B 6/4266; A61B 6/461; A61B 6/032; A61B 6/405
See application file for complete search history.

(56) References Cited

U.S. PATENT DOCUMENTS 5,590,164 A    12/1996  Kawai et al.
2013/0223585 A1*  8/2013  Tsukagoshi .......... G01N 23/046
                                                  378/4
2018/0199898 A1*  7/2018  Zhang ...................... A61B 6/00

FOREIGN PATENT DOCUMENTS

JP     8-10251          1/1996
JP     2009-89810       4/2009
WO     WO-2017107179 A1 *  6/2017 ............... A61B 6/00

* cited by examiner

*Primary Examiner* — Kiho Kim
(74) *Attorney, Agent, or Firm* — Oblon, McClelland, Maier & Neustadt, L.L.P.

(57) ABSTRACT

According to one embodiment, an X-ray computed tomography apparatus includes an X-ray tube, an X-ray detector, and control circuitry. The X-ray tube generates X-rays. The X-ray detector includes a plurality of X-ray detection elements that detect X-rays generated by the X-ray tube. The control circuitry adjusts a position of an X-ray path with respect to the respective X-ray detection elements based on either the first mode for generating an image having the first resolution, or the second mode for generating an image having the second resolution lower than the first resolution.

14 Claims, 11 Drawing Sheets

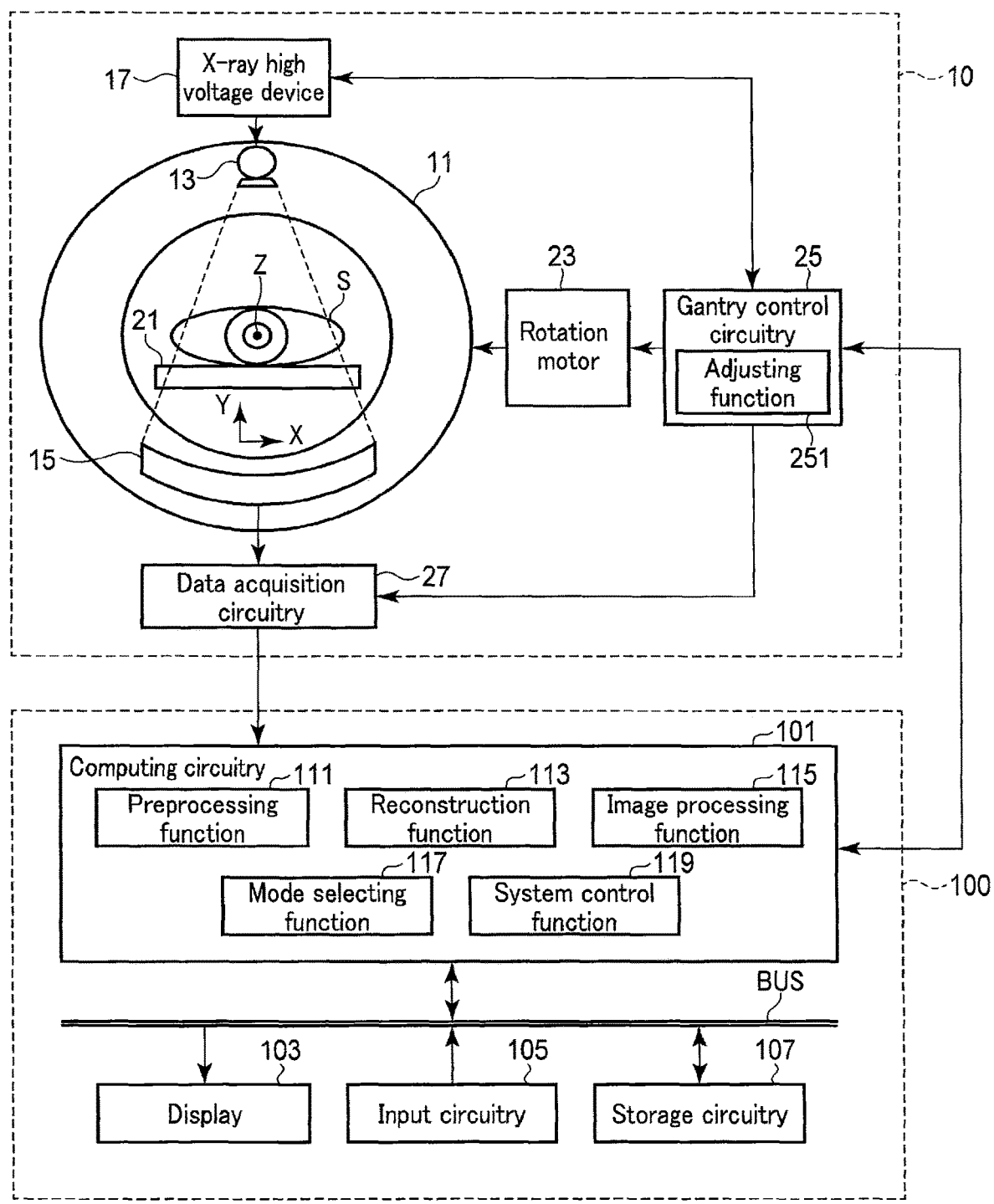
F I G. 1

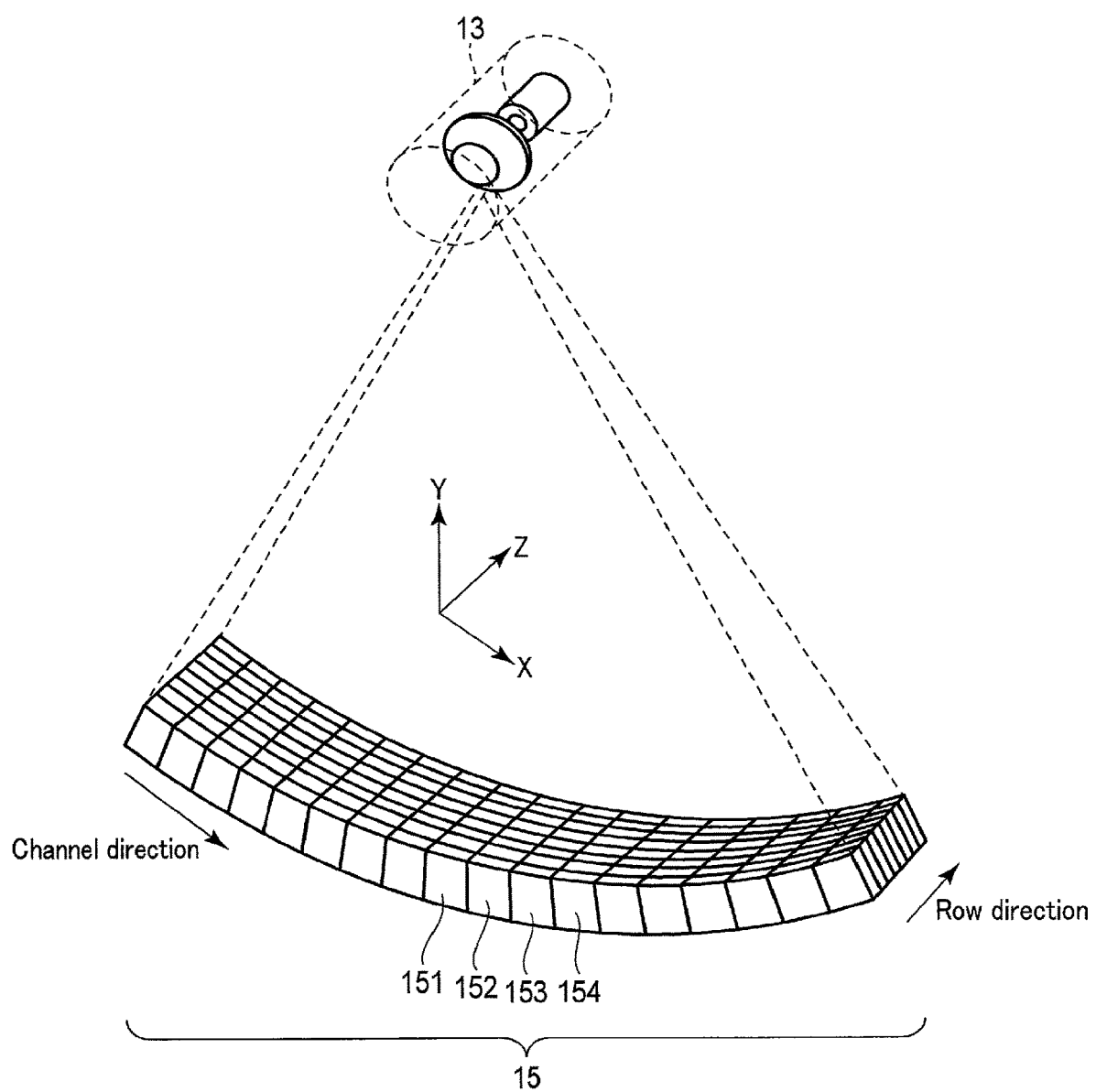
F I G. 4

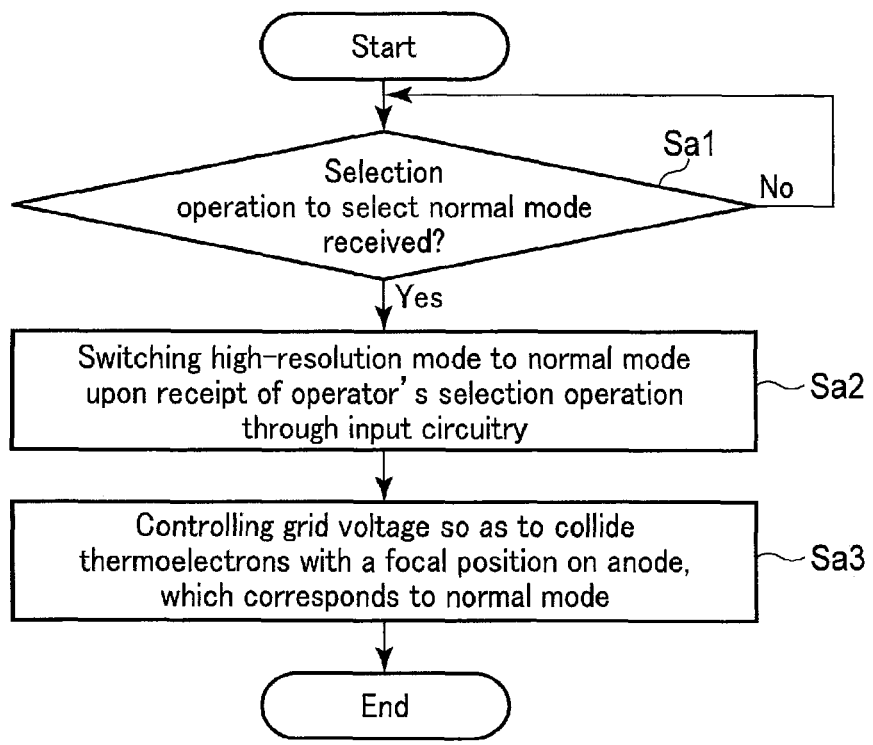
F I G. 7
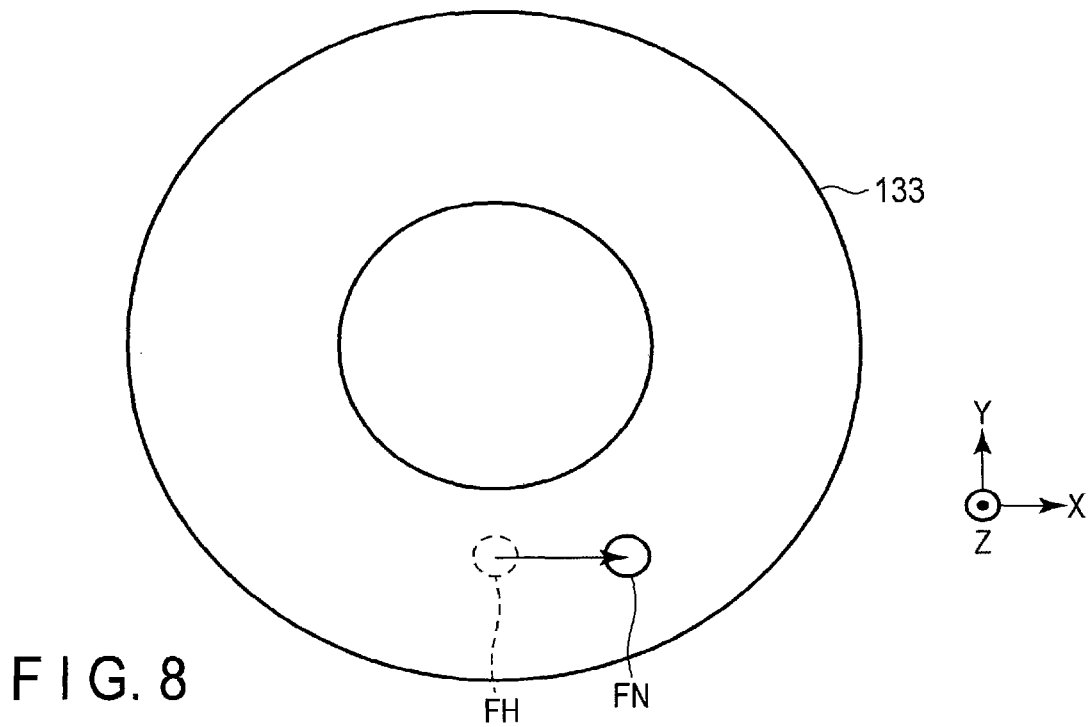
F I G. 8

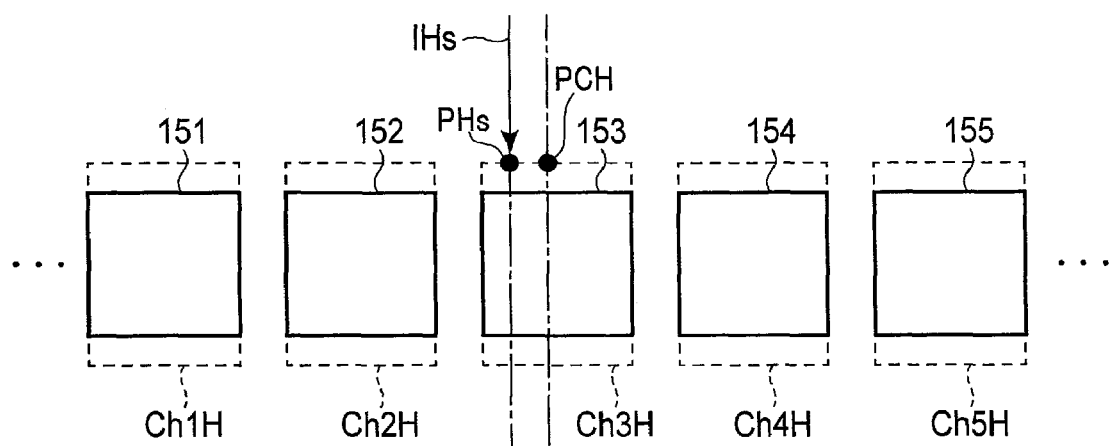
F I G. 9A
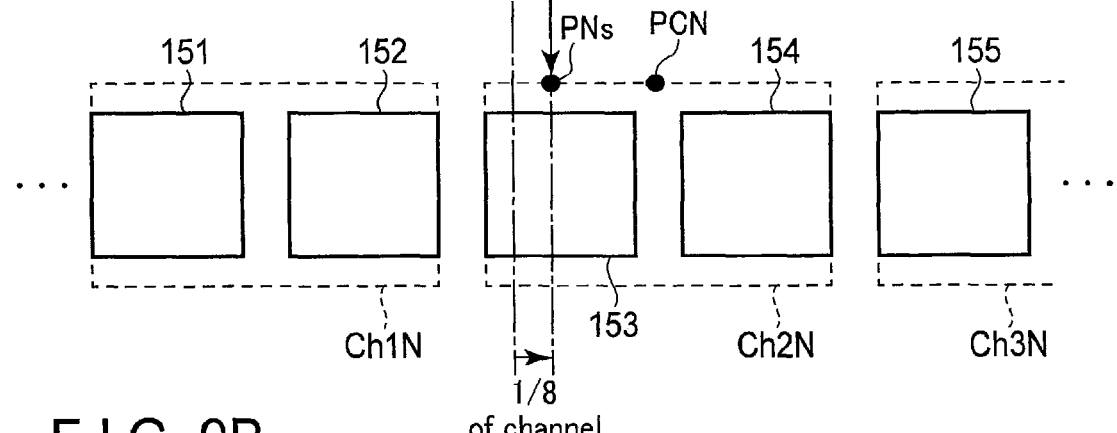
F I G. 9B

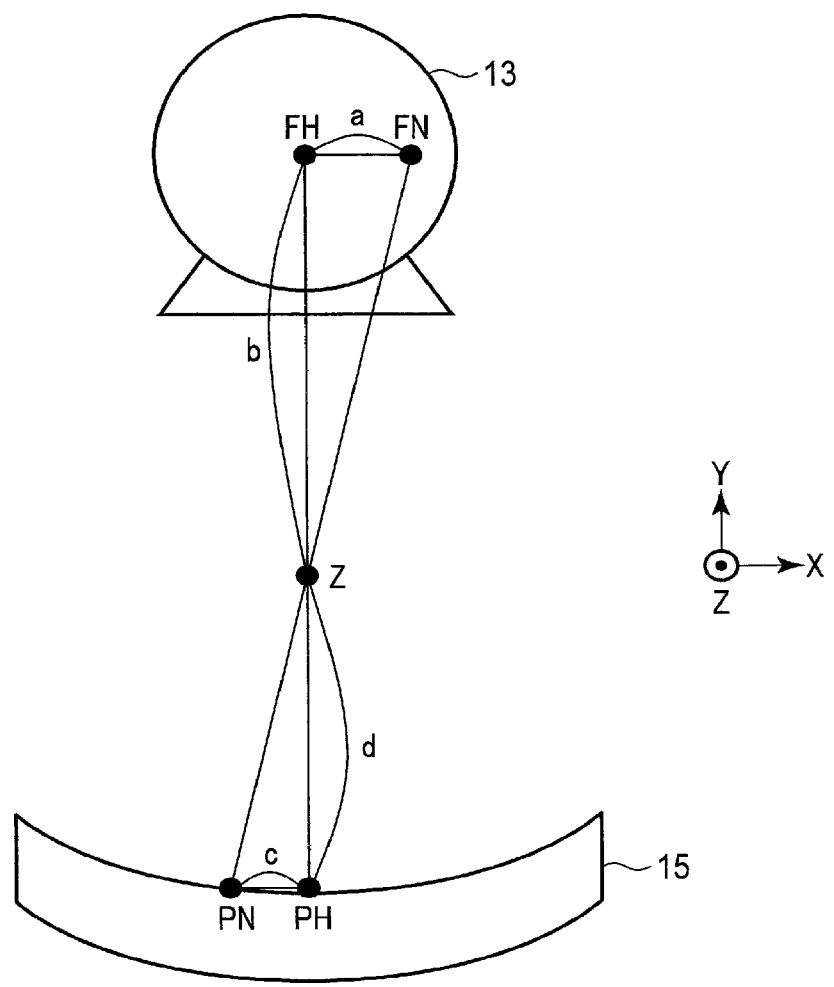
F I G. 10

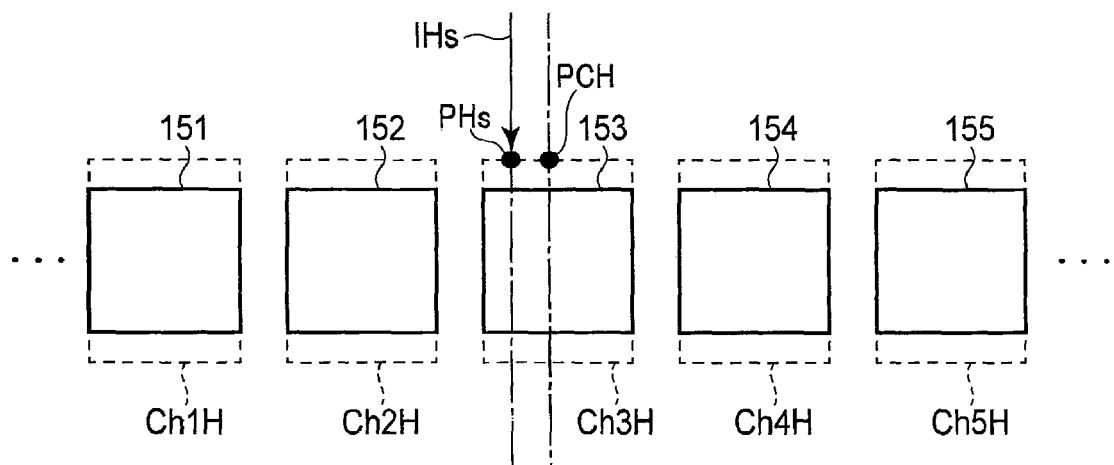
F I G. 11A
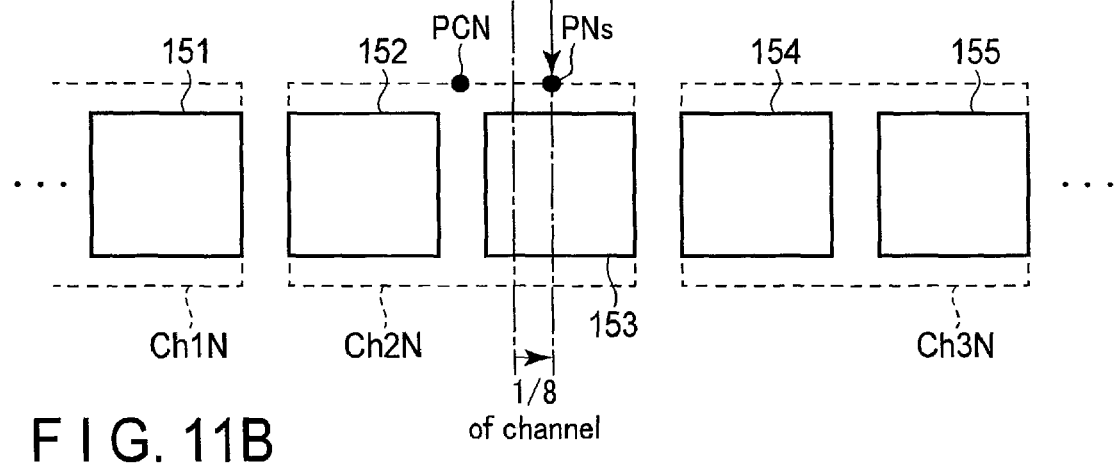
F I G. 11B

X-RAY COMPUTED TOMOGRAPHY APPARATUS

CROSS-REFERENCE TO RELATED APPLICATIONS

This application is based upon and claims the benefit of priority from the Japanese Patent Application No. 2017-170461, filed Sep. 5, 2017 the entire contents of which are incorporated herein by reference.

FIELD

Embodiments described herein relate generally to an X-ray computed tomography apparatus.

BACKGROUND

X-ray computed tomography (CT) apparatuses are each provided with an X-ray detector that includes a plurality of X-ray detection elements. In some cases, X-ray detection elements are arranged in positions shifted by ¼ of a channel in a channel direction. This is called a ¼ offset arrangement.

The recent development of X-ray CT apparatuses has realized selective use of a plurality of detector resolution modes such as a normal mode for generating images with a normal resolution and a high-resolution mode for generating images with a higher resolution than the normal mode. This type of X-ray CT apparatus changes units of a channel that outputs X-ray detection signals according to each mode. For example, in a high-resolution mode, the X-ray CT apparatus outputs X-ray detection signals from X-ray detection elements, while setting a single channel to each of X-ray detection elements. In a normal mode, the X-ray CT apparatus causes the X-ray detection elements to output X-ray detection signals, while setting a single channel to a predetermined number of adjacent X-ray detection elements. For example, in the normal mode, the X-ray CT apparatus classifies two X-ray detection elements as a single channel.

In this case, a position of a channel's center varies between the high-resolution mode and the normal mode. For example, if the X-ray detection elements are arranged ¼-offset under the high-resolution mode, their shift amount turns out to be as little as ⅛ of a channel under the normal mode. That is, a ¼-offset arrangement of X-ray detection elements is unrealizable in the normal mode. Therefore, if the X-ray detection elements are arranged ¼-offset in accordance with the high-resolution mode, the resolution of images generated in the normal mode is deteriorated as compared with the case where the X-ray detection elements are arranged ¼-offset in accordance with the normal mode.

BRIEF DESCRIPTION OF THE DRAWINGS

FIG. 1 is a block diagram showing the configuration of an X-ray CT apparatus according to the present embodiment.

FIG. 4 is a perspective view of an X-ray detector shown in FIG. 1.

FIG. 7 is a flowchart showing how the X-ray CT apparatus according to the present embodiment operates in the case of switching from the high-resolution mode to the normal mode.

FIG. 8 is a view showing a focal position according to the high-resolution mode according to FIG. 7 and a focal position according to the normal mode.

FIGS. 9A and 9B are views each showing a positional relationship of an X-ray path with respect to X-ray detection elements and channels in the case of switching from the high-resolution mode to the normal mode.

FIG. 10 is a view showing an example of how to calculate a motion distance of a focal point shown in FIG. 8.

FIGS. 11A and 11B are views each showing another positional relationship of an X-ray path with respect to X-ray detection elements and channels in the case of switching from the high-resolution mode to the normal mode.

DETAILED DESCRIPTION

Figure 2:
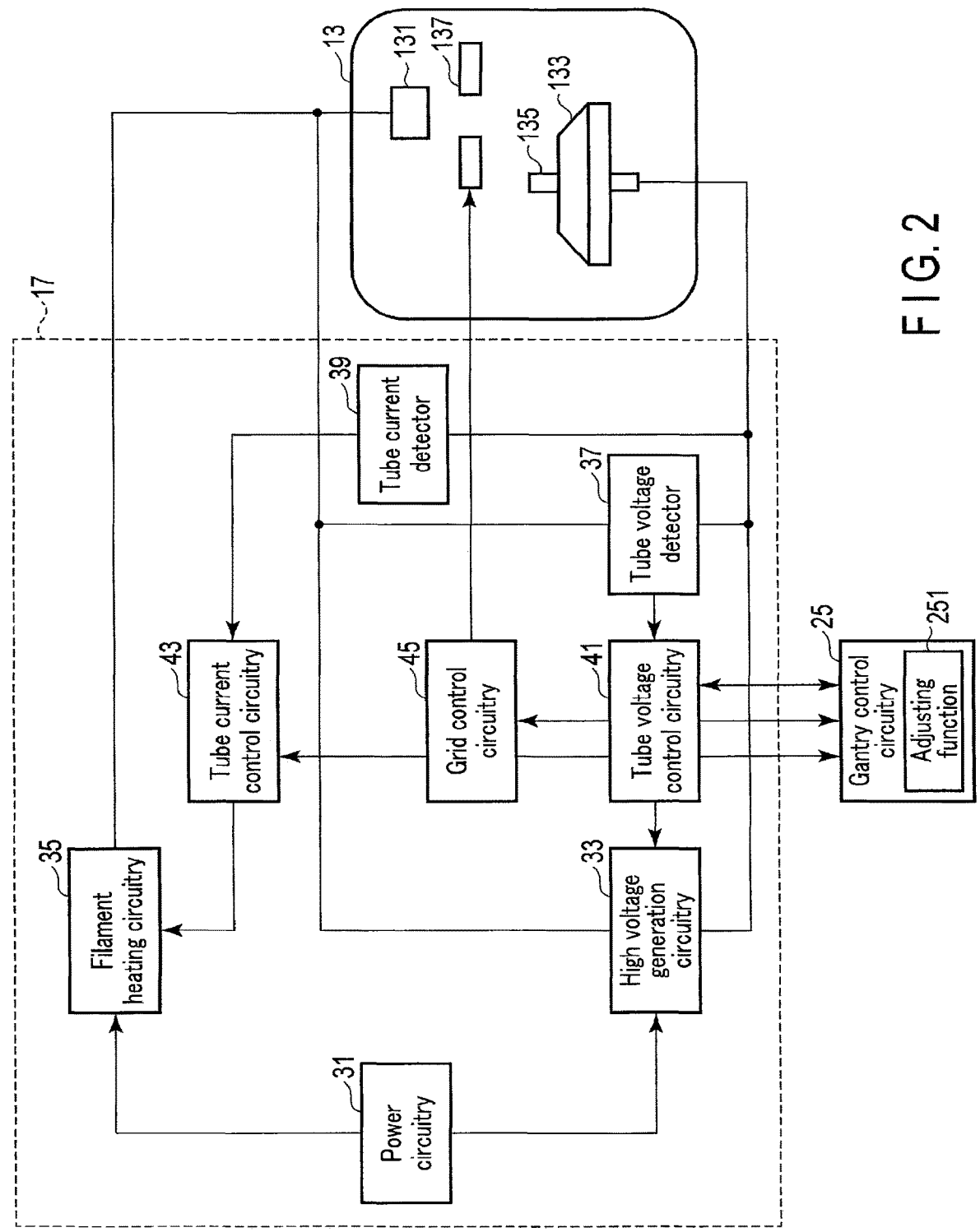
FIG. 2 illustrates the configuration of an X-ray tube and an X-ray high voltage device shown in FIG. 1.

In general, according to one embodiment, an X-ray computed tomography apparatus includes an X-ray tube, an X-ray detector, and control circuitry. The X-ray tube generates X-rays. The X-ray detector includes a plurality of X-ray detection elements that detect X-rays generated by the X-ray tube. The control circuitry adjusts a position of an X-ray path with respect to the X-ray detection elements based on either a first mode for generating an image having a first resolution, or a second mode for generating an image having a second resolution lower than the first resolution.

Hereinafter, an X-ray CT apparatus according to the present embodiment will be described with reference to the drawings.

(Configuration of X-ray CT Apparatus)

FIG. 1 is a block diagram showing the configuration of an X-ray CT apparatus according to the present embodiment. In the X-ray CT apparatus shown in FIG. 1, an X-ray generation source applies X-rays to subject S, and an X-ray detector detects X-rays applied by the X-ray generation source. The X-ray CT apparatus generates a CT image regarding the subject S based on output from the X-ray detector.

The X-ray CT apparatus shown in FIG. 1 includes a gantry device 10 and a console 100. For example, the gantry device 10 is placed in a CT examination room, and the console 100 is placed in a control room adjacent to the CT examination room. A control room to place the console 100 is not necessarily required, and the gantry device 10 and the console 100 may be placed in the same room. The gantry device 10 and the console 100 are communicatively connected to each other through wire or radio. The gantry device 10 is a scanner having a configuration for X-ray CT imaging of the subject S. The console 100 is a computer that controls the gantry device 10.

(Description of Gantry Device)

Hereinafter, each configuration of the X-ray CT apparatus according to the present embodiment will be described with reference to FIG. 1. First, the gantry device 10 according to the present embodiment will be described.

As shown in FIG. 1, the gantry device 10 includes a rotation frame 11, the tabletop 21, an X-ray tube 13, an X-ray detector 15, an X-ray high voltage device 17, a Data Acquisition System (DAS) 27, and a gantry control circuitry 25.

The rotation frame 11 is a housing in an approximately cylindrical shape, in which a bore is formed as an imaging space. The bore substantially corresponds to a Field of View (FOV). As shown in FIG. 1, the X-ray tube 13 and the X-ray detector 15, which are arranged to face each other with the bore interposed therebetween, are attached to the rotation frame 11. The rotation frame 11 is a metal frame made, for example, of aluminum, in an annular shape. In further detail, the gantry device 10 includes a main frame (not shown) made of metal such as aluminum. The rotation frame 11 is supported by this main frame via a bearing and the like to be rotatable about a center axis Z. In the following description about the X-ray CT apparatus according to the present embodiment, a Z-axis direction represents a body axis direction of the subject S, a Y-axis direction represents a vertical direction of the subject S, and an X-axis direction represents a direction perpendicular to the Z-axis and the Y-axis.

The rotation frame 11 rotates about the center axis Z at a predetermined angular speed upon receiving power from a rotation motor 23. Under control of the gantry control circuitry 25, the rotation motor 23 generates power to rotate the rotation frame 11. The rotation motor 23 generates power by being driven at a rotation speed corresponding to a duty ratio, etc. of a driving signal from the gantry control circuitry 25. The rotation motor 23 is implemented by, for example, a motor such as a direct drive motor, a servo motor, etc. The rotation motor 23 is stored in, for example, the gantry device 10.

The tabletop 21 is inserted into the bore of the rotation frame 11. The subject S is placed on the tabletop 21. The tabletop 21 is positioned in a manner so that an imaging target of the subject S placed on the tabletop 21 is contained in the FOV. The tabletop 21 is supported in a movable manner along the center axis Z of the rotation frame 11. The tabletop 21 is positioned in a manner so that the body axis of the subject S placed on the tabletop 21 corresponds to the center axis Z of the rotation frame 11.

Under control of the console 100 through the gantry control circuitry 25, the X-ray high voltage device 17 generates a tube voltage to apply to the X-ray tube 13 and a filament current to supply to the X-ray tube 13. The X-ray high voltage device 17 may adopt an X-ray high voltage device of any type, such as a variable voltage type, a constant voltage type, a capacitive type, or an inverter type. The X-ray high voltage device 17 of, for example, an inverter type includes an inverter and a high voltage converter. The inverter switches a direct current (DC) from a power circuitry 31 to be described later at a timing under control of tube voltage control circuitry 41, thereby making conversion to an alternating output pulse. The high voltage converter converts the alternating output pulse from the inverter into a DC high voltage.

The X-ray tube 13 is connected to the X-ray high voltage device 17 via a high voltage cable (not shown). Upon receiving the application of a tube voltage and supply of a filament current from the X-ray high voltage device 17, the X-ray tube 13 generates X-rays to apply to the subject S placed on the tabletop 21.

The X-ray detector 15 detects X-rays generated by the X-ray tube 13 and transmitted through the subject S. The X-ray detector 15 includes a plurality of X-ray detection elements (not shown) arrayed on a two-dimensional curved surface. Each of the X-ray detection elements detects X-rays from the X-ray tube 13 and converts them into electrical signals having a peak value according to the intensity of the detected X-rays. Each of the X-ray detection elements includes, for example, a scintillator and a photoelectric converter. Upon receipt of X-rays, the scintillator generates fluorescence. The photoelectric converter converts the fluorescence generated by the scintillator into a charge pulse. The charge pulse has a peak value according to the intensity of X-rays. As the photoelectric converter, a circuit element that converts photons into electrical signals, such as a photomultiplier or a photodiode, is used. The X-ray detector 15 according to the present embodiment is not limited to a detector of an indirect-convert type that temporarily converts an X-ray into fluorescence and then converts it into an electrical signal, and may be a detector (semiconductor detector) of a direct-convert type that directly converts an X-ray into an electrical signal. The X-ray detector 15 is connected to the data acquisition circuitry 27.

The data acquisition circuitry 27 acquires, for each view, digital data representing the intensity of X-ray attenuated by the subject S. The data acquisition circuitry 27 acquires electrical signals from the plurality of X-ray detection elements and bundles the acquired electrical signals in bundle units in accordance with each detector resolution mode of the X-ray detector 15 to be described later. The data acquisition circuitry 27 is implemented by, for example, a semiconductor integrated circuitry on which an integrator, an amplifier, and an A/D converter provided in correspondence with each of the plurality of X-ray detection elements are implemented in parallel. The data acquisition circuitry 27 is connected to the X-ray detector 15 within the gantry device 10. The integrator integrates electrical signals from an X-ray detection element during a predetermined view period to generate an integral signal. The amplifier amplifies the integral signal output by the integrator. The A/D converter A/D converts the 1 amplified integral signal to generate digital data having a data value corresponding to the peak value of the integral signal. The digital data after conversion is called raw data. Raw data is a set of digital values of X-ray intensity identified by the channel number, the column number, and the view number of an X-ray detection element as the generation source. The data acquisition circuitry 27 supplies raw data to the console 100 via, for example, non-contact data transmission circuitry (not shown) housed in the gantry device 10.

The gantry control circuitry 25 includes, as hardware resources, a processor such as a Central Processing Unit (CPU) or a Micro Processing Unit (MPU), and a memory such as a Read Only Memory (ROM) or a Random Access Memory (RAM). The gantry control circuitry 25 may be implemented by an Application Specific Integrated Circuit (ASIC) or a Field Programmable Gate Array (FPGA), another Complex Programmable Logic Device (CPLD), or a Simple Programmable Logic Device (SPLD). In compliance with the instructions from the console 100, the gantry control circuitry 25 controls the X-ray high voltage device 17, the rotation motor 23, and the data acquisition circuitry 27. The processor implements the above function by reading and executing a program stored in the memory.

For example, the gantry control circuitry 25 according to the present embodiment implements an adjusting function 251 by executing a program. By the adjusting function 251, the gantry control circuitry 25 adjusts the position of an X-ray path with respect to the plurality of X-ray detection elements based on either the first detector resolution mode for generating an image having the first resolution, or the second detector resolution mode for generating an image having the second resolution lower than the first resolution. Specifically, the gantry control circuitry 25 controls a grid voltage to apply to a grid described later, in order to change a position (hereinafter referred to as "focal position") where thermoelectrons collide, in accordance with a detector resolution mode. Instead of storing a program on the memory, the program may be directly integrated into the circuitry of the processor. In this case, the processor implements the above function by reading and executing the program integrated into the circuitry.

(Description of Console)

Next, the console 100 according to the present embodiment will be described. The console 100 shown in FIG. 1 includes computing circuitry 101, a display 103, input circuitry 105, and storage circuitry 107. Data communication is performed between the computing circuitry 101, the display 103, the input circuitry 105, and the storage circuitry 107 via a bus.

The computing circuitry 101 includes, as hardware resources, a processor such as a CPU, an MPU, or a Graphics Processing Unit (GPU), and a memory such as a ROM or a RAM. The computing circuitry 101 executes various programs to implement a preprocessing function 111, a reconstruction function 113, an image processing function 115, a mode selecting function 117, and a system control function 119.

By the preprocessing function 111, the computing circuitry 101 performs preprocessing such as a logarithmic conversion to raw data transmitted from the gantry device 10. The preprocessed raw data is referred to as projection data. By the reconstruction function 113, the computing circuitry 101 reconstructs a CT image representing a space distribution of CT values relating to the subject S based on the projection data generated by the preprocessing function 111. The computing circuitry 101 reconstructs a CT image in consideration of a position shift amount in an X-ray path in accordance with each of detector resolution modes to be described later. As an image reconstruction algorithm, a known image reconstruction algorithm such as a Filtered Back Projection (FBP) method or a successive approximation reconstruction method may be adopted.

By the image processing function 115, the computing circuitry 101 performs various image processing on the CT image reconstructed by the reconstruction function 113. For example, the computing circuitry 101 generates a display image by performing three-dimensional image processing, such as volume rendering, surface rendering, image value projection processing, Multi-Planer Reconstruction (MPR) processing, Curved MPR (CPR) processing, etc. on the CT image.

By the mode selecting function 117, the computing circuitry 101 causes the display 103 to display a selection window through which one of detector resolution modes is selected. The detector resolution modes according to the present embodiment include a high-resolution mode (first mode) to generate an image having a high resolution (first resolution) and a normal mode (second mode) to generate an image having a normal resolution (second resolution). The computing circuitry 101 causes the display 103 to display a selection screen through which one of the high-resolution mode and the normal mode is selected.

By the system control function 119, the computing circuitry 101 comprehensively controls the X-ray CT apparatus according to the present embodiment. Specifically, the computing circuitry 101 reads a control program stored in the storage circuitry 107, expands the control program in a memory, and controls the respective units of the X-ray CT apparatus in accordance with the expanded control program. For example, upon receipt of an operator's selection operation to select the high-resolution mode or the normal mode through the input circuitry 105, the computing circuitry 101 instructs the gantry control circuitry 25 to control a grid voltage to apply to a grid described later, in accordance with the selected mode.

The preprocessing function 111, the reconstruction function 113, the image processing function 115, the mode selecting function 117, and the system control function 119 may be implemented by the computing circuitry 101 on a single substrate, or may be implemented by the computing circuitry 101 on a plurality of substrates.

The display 103 displays various types of data, the aforementioned medial image, etc. Specifically, the display 103 includes a display interface and a display device. The display interface converts data representing a display target into a video signal. The video signal is supplied to the display device. The display device displays a video signal representing a display target. For example, a Cathode Ray Tube (CRT) display, a Liquid Crystal Display (LCD), an Organic Electro Luminescence Display (OELD), a plasma display, or any other displays known in this technical field can be appropriately utilized as the display device.

The input circuitry 105 receives various instructions from an operator. Specifically, the input circuitry 105 includes an input device and an input interface. The input device receives various instructions from a user. The input device can be implemented by a trackball, a scroll wheel, a switch button, a mouse, a keyboard, a touch pad through which an input operation is carried out by touching an operation surface, a touch panel display having a display screen and a touch pad integrated as one unit, etc. The input interface supplies an output signal from the input device to the computing circuitry 101 via a bus. In the present embodiment, the input circuitry 105 is not limited to circuitry that includes physical operation components such as a trackball, a scroll wheel, a switch button, a mouse, a keyboard, etc. Examples of the input circuitry 105 include electrical signal processing circuitry that receives an electrical signal corresponding to operation input through an external input device provided independently of the apparatus, and outputs the electrical signal to the computing circuitry 101.

The storage circuitry 107 is a storage device such as a Hard Disk Drive (HDD), a Solid State Drive (SSD), or an integrated circuit storage device, which stores various types of information. Other than an HDD, SSD, etc., the storage circuitry 107 may be a driving device which reads and writes various types of information to and from a portable storage medium such as a Compact Disc (CD), a Digital Versatile Disc (DVD), a flash memory, etc. The storage circuitry 107 may have its storage area within the X-ray CT apparatus or a network-connected external storage device. For example, the storage circuitry 107 stores data on a CT image or a display image. The storage circuitry 107 further stores, e.g., a control program according to the present embodiment.

(Description of X-Ray Tube and X-Ray High Voltage Device)

Figure 3:
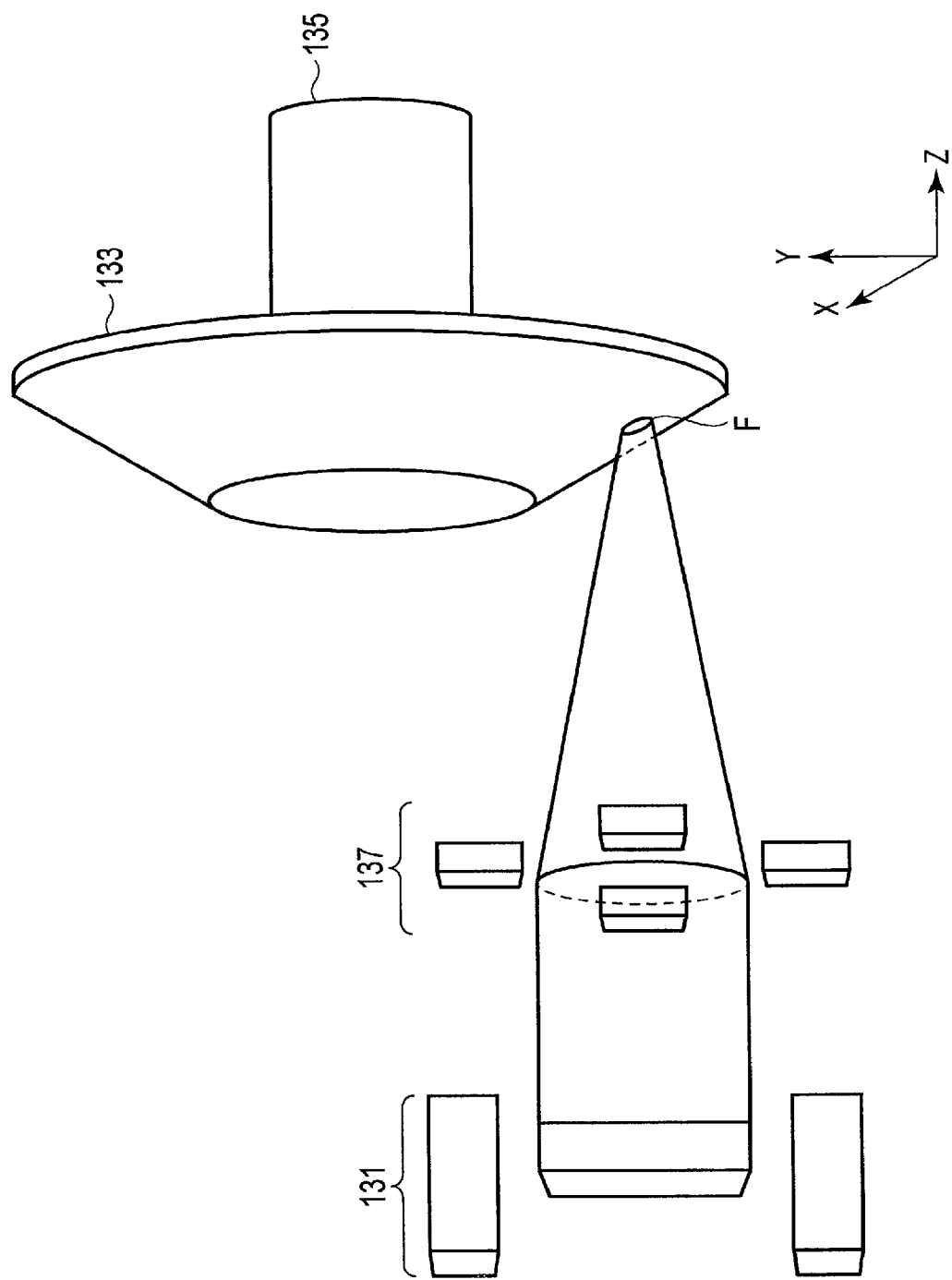
FIG. 3 illustrates thermoelectrons emitted from a cathode shown in FIG. 2, and a focal position of thermoelectrons that are converged by a grid and collide with an anode.

Hereinafter, the configuration of the X-ray tube 13 and the X-ray high voltage device 17 will be further described with reference to FIGS. 2 to 4. FIG. 2 illustrates the configuration of the X-ray tube 13 and the X-ray high voltage device 17 shown in FIG. 1. As shown in FIG. 2, the X-ray tube 13 houses a cathode 131, an anode 133, a rotor 135, and a grid 137. The inside of the X-ray tube 13 that houses the cathode 131, the anode 133, the rotor 135, and the grid 137 is maintained as a vacuum.

The cathode 131 is made of metal in a a narrow linear shape or a plate shape. The following description is premised on the cathode 131 that is a filament made of metal such as tungsten, nickel, etc., in a narrow linear shape. The cathode 131 is connected to the X-ray high voltage device 17 via a high voltage cable, etc. The cathode 131 generates heat and emits thermoelectrons upon receipt of a filament heating current supplied from the X-ray high voltage device 17.

The anode 133 is an electrode in a disc shape. The anode 133 is also referred to as a target. The anode 133 is made of heavy metal such as tungsten, molybdenum, etc. The rotor 135 is attached to the anode 133. The anode 133 rotates as the rotor 135 rotates about its axis. The anode 133 and the rotor 135 form a rotating anode. The X-ray high voltage device 17 applies a tube voltage between the cathode 131 and the anode 133. Thermoelectrons emitted from the cathode 131 are accelerated while being converged as a beam by the tube voltage applied between the cathode 131 and the anode 133, thereby colliding with the anode 133 in rotation. The anode 133 generates X-rays upon receipt of thermoelectrons from the cathode 131.

The grid 137 is arranged between the cathode 131 and the anode 133. The grid 137 electrically or magnetically adjusts a trajectory of thermoelectrons traveling from the cathode 131 to the anode 133, and a focus size of the thermoelectrons on the surface of anode 133. The grid 137 may be any hardware which electrically or magnetically deflects a trajectory and a focus size of thermoelectrons. For example, the grid 137 may be realized by an electrode, a magnet, a coil, etc. The following description is premised on the grid 137 realized by an electrode. The grid 137 deflects a trajectory of thermoelectrons traveling from the cathode 131 to the anode 133 and regulates a focus size upon receipt of a voltage (grid voltage) applied from the X-ray high voltage device 17.

Under control of the control of gantry control circuitry 25, the X-ray high voltage device 17 applies a tube voltage to the X-ray tube 13 and supplies a filament heating current. The X-ray high voltage device 17 deflects a trajectory of thermoelectrons traveling from the cathode 131 to the anode 133 and regulates a focus size on the anode 133, of thermoelectrons from the cathode 131 housed in the X-ray tube 13. Specifically, the X-ray high voltage device 17 includes power circuitry 31, a high voltage generation circuitry 33, filament heating circuitry 35, a tube voltage detector 37, a tube current detector 39, tube voltage control circuitry 41, tube current control circuitry 43, and grid control circuitry 45.

The power circuitry 31 generates DC based on an alternating current (AC) from a power supply system installed in, e.g., a CT examination room provided with the gantry device 10. Specifically, the power circuitry 31 includes rectifying circuitry and a smoothing capacitor. The rectifying circuitry rectifies AC from the power supply system into DC. The smoothing capacitor smoothes the AC rectified by the rectifying circuitry. By this rectification and smoothing, AC is converted into DC. A power source to supply power to the power circuitry 31 is not limited to a power supply system, and may be a capacitor or a storage battery.

The high voltage generation circuitry 33 generates a tube voltage to apply to the X-ray tube 13 under control of the tube voltage control circuitry 41. The high voltage generation circuitry 33 and the anode 133 are connected by an anode side high voltage cable, and the high voltage generation circuitry 33 and the cathode 131 are connected by a cathode side high voltage cable.

The filament heating circuitry 35 generates power to heat the cathode 131 under control of the tube current control circuitry 43. The filament heating circuitry 35 may adopt either a variable resistance type or a high frequency heating type. For example, the filament heating circuitry 35 of a high frequency heating type includes an inverter and a filament heating transformer. The inverter switches DC from the power circuitry 31 at a timing under control of the tube voltage control circuitry, thereby making conversion into an alternating output pulse. The filament heating transformer transforms the alternating output pulse from the inverter into a DC filament heating current.

The tube voltage detector 37 is connected between the anode side high voltage cable and the cathode side high voltage cable. The tube voltage detector 37 detects a tube voltage applied between the cathode 131 and the anode 133. Data on a value of the detected tube voltage (hereinafter, referred to as "tube voltage detection value") is supplied to the tube voltage control circuitry 41.

The tube current detector 39 is connected to the anode side high voltage cable. The tube current detector 39 detects, as a tube current, a current that has flowed to the anode side high voltage cable due to thermoelectrons flowing from the cathode 131 to the anode 133. Data on a value of the detected tube current (hereinafter, referred to as "tube current detection value") is supplied to the tube current control circuitry 43.

The tube voltage control circuitry 41 controls the high voltage generation circuitry 33 based on a comparison between the tube voltage detection value and a set tube voltage value. In further detail, the tube voltage control circuitry 41 compares the tube voltage detection value with the set tube voltage value, and performs feedback control to the high voltage generation circuitry 33 so that the tube voltage detection value converges to the set tube voltage value. Data on the set tube voltage value is supplied from the gantry control circuitry 25. The tube voltage control circuitry 41 transmits, to the gantry control circuitry 25, data on the tube voltage detection value detected by the tube voltage detector 37.

The tube current control circuitry 43 controls the filament heating circuitry 35 based on a comparison between the tube current detection value and the set tube current value. More specifically, the tube current control circuitry 43 compares the tube current detection value with the set tube current value, and performs feedback control to the filament heating circuitry 35 so that the tube current detection value converges to the set tube current value. Data on the set tube current value is supplied from the gantry control circuitry 25. The tube current control circuitry 43 transmits data on the tube current detection value detected by the tube current detector 39, to the gantry control circuitry 25.

The grid control circuitry 45 controls a grid voltage to apply to the grid 137, in order to change in accordance with a selected mode, a focal position on the anode 133 in which thermoelectrons emitted from the cathode 131 collide. FIG. 3 illustrates thermoelectrons emitted from the cathode 131 shown in FIG. 2, and a focal position F of the thermoelectrons that are converged by the grid 137 and collide with the anode 133. Specifically, the grid control circuitry 45 stores in memory, etc., bias voltage values corresponding to focal positions according to predetermined modes, respectively. In scanning, if the gantry control circuitry 25 supplies a signal indicative of a status that scanning is being performed, the grid control circuitry 45 reads from a memory a bias voltage value corresponding to a focal position according to a selected mode. The grid control circuitry 45 applies to the grid 137 a voltage corresponding to the read bias voltage value. This enables thermoelectrons from the cathode 131 to collide with the focal position F according to a selected mode, as shown in FIG. 3.

The tube voltage control circuitry 41, the tube current control circuitry 43, and the grid control circuitry 45 may be mounted in a single substrate or in a plurality of substrates. In addition, the tube voltage control circuitry 41, the tube current control circuitry 43, and the grid control circuitry 45 may be implemented by analog circuitry or digital circuitry. If the tube voltage control circuitry 41, the tube current control circuitry 43, and the grid control circuitry 45 are implemented as digital circuitry, they include, as hardware resources, a processor such as a CPU or a MPU, and memory such as a ROM or a RAM. The tube voltage control circuitry 41, the tube current control circuitry 43, and the grid control circuitry 45 may be realized by an ASIC, an FPGA, a CPLD, an SPLD, etc.

As one example of the X-ray tube 13, FIG. 2 shows the configuration of the X-ray tube of a rotating anode type. However, the present embodiment is not limited to this configuration. As the X-ray tube 13, the X-ray CT apparatus according to the present embodiment may adopt an X-ray tube of a fixed anode type, for example.

(Description of X-Ray Detector)

FIG. 4 is a perspective view of the X-ray detector 15 shown in FIG. 1. The X-ray detector 15 according to the present embodiment is switchable in terms of its resolution regarding the channel direction and the row direction. The detector resolution modes are classified into the high-resolution mode and the normal mode. The high resolution mode and the normal mode are electrically switchable by the gantry control circuitry 29, etc. As shown in FIG. 4, the X-ray detector 15 has a plurality of X-ray detection elements arrayed in the channel direction (the direction of rotation around the center axis Z of rotation) and a plurality of X-ray detection elements arrayed in the row direction (Z-axis direction). The X-ray detection elements are arranged in positions shifted by a predetermined distance in the channel direction with reference to a channel's center. The predetermined distance is typically ¼ of an element width. This is called a ¼-offset arrangement. This arrangement is to reduce aliasing and to improve the spatial resolution. A plurality of X-ray detection elements according to the present embodiment are those for high resolution.

The X-ray detector 15 according to the present embodiment may be a multi-row detector such as shown in FIG. 4 or a single-row detector having a single row of X-ray detection elements. In the case of the X-ray detector 15 being a multi-row detector, the number of X-ray detection elements arrayed in the channel direction and the number of rows of X-ray detection elements arrayed in the row direction may be set as appropriate.

Hereinafter, a relationship between a channel's center and an X-ray path applied from the X-ray tube 13 in each mode will be described with reference to FIGS. 5 and 6. In the present embodiment, as an example, a relationship between a channel's center and an X-ray path in a plurality of X-ray detection elements 151-154 shown in FIG. 4 will be described. A channel indicates a bundle unit of X-ray detection elements when an electrical signal is read from the X-ray detection elements. A center element indicates the X-ray detection element positioned in the center in the channel direction of the X-ray detection elements mounted in the X-ray detector 15. The center element is the X-ray detection element that intersects the center axis of X-ray generated by the X-ray tube 13. A center channel indicates the channel positioned in the center in the channel direction of the plurality of channels. The center in the channel direction of each channel is referred to as a channel's center. An X-ray path indicates a path of X-rays which connects a focal point on the anode 133 included in the X-ray tube 13 with the respective X-ray detection elements. The X-ray path is presented by the center axis of X-ray which is generated by the X-ray tube 13 and passes through the center axis Z.

Figure 5:
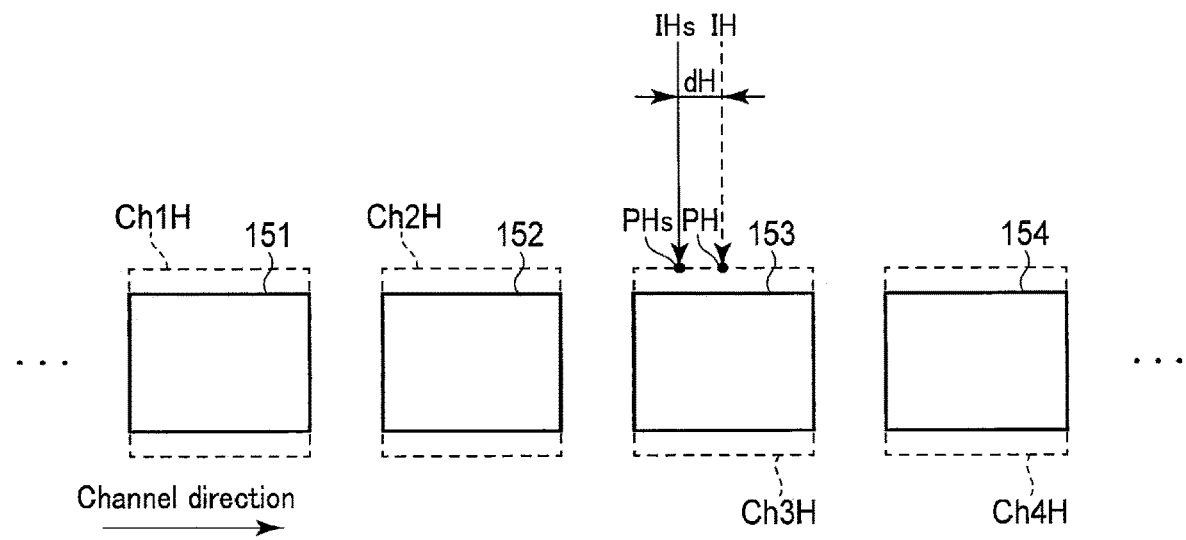
FIG. 5 is a view showing a relationship between a channel's center and an X-ray path applied from the X-ray tube in a high-resolution mode.

FIG. 5 is a view showing a relationship between a channel's center and an X-ray path in a high-resolution mode. In the high-resolution mode, channels ChnH ("n" represents an integer) are set to the X-ray detection elements 15$n$ ("n" represents an integer), respectively. If the X-ray detection elements are not arranged ¼-offset, X-ray path IH passes through center PH of center channel Ch3H in the high-resolution mode. In the high-resolution mode, if the X-ray detection elements 151-154 are arranged in positions shifted by predetermined distance dH from the channel's center PH in the channel direction, X-ray path IHs passes through position PHs which is shifted by the distance dH from the center PH in the channel direction on the center channel Ch3H.

The shift amount (distance dH) of the X-ray detection elements in the high-resolution mode is equal to ¼ of a channel width in the high-resolution mode (that is, a width of a single X-ray detection element in the high-resolution mode). For example, if a single X-ray detection element has a width of 1 mm, the distance dH is expressed as "dH=1 mm×¼=0.25 mm".

Figure 6:
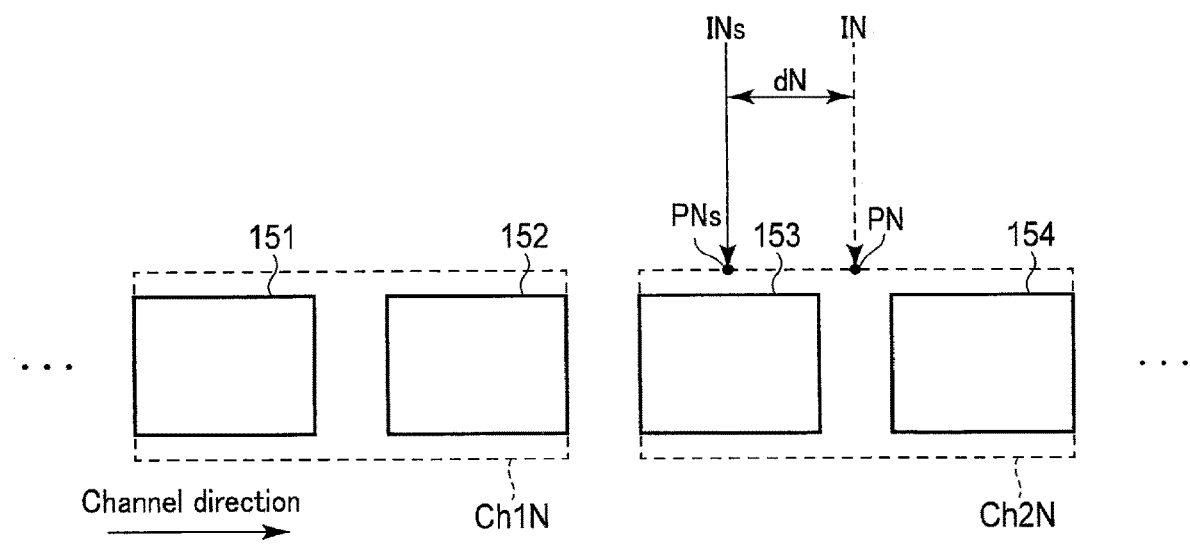
FIG. 6 is a view showing a relationship between a channel's center and an X-ray path applied from the X-ray tube in a normal mode.

FIG. 6 is a view showing a relationship between a channel's center and an X-ray path in a normal mode. Under the normal mode, the adjacent two X-ray detection elements 15$n$ ("n" represents an integer) form a single channel ChnN ("n" represents an integer). Herein, assume that the X-ray detection element 153 positioned in the channel's center and the X-ray detection element 154 positioned after the X-ray detection element 153 in the channel direction form center channel Ch2N. If the X-ray detection elements are not arranged ¼-offset, X-ray path IN passes through center PN of the center channel Ch2N in the normal mode. In the normal mode, if the X-ray detection elements 151-154 are arranged in positions shifted by predetermined distance dN from the channel's center PN in the channel direction, X-ray path INs passes through position PNs of the center channel Ch2N. As described later, the X-ray detection element 153 positioned in the channel's center and the X-ray detection element 152 positioned before the X-ray detection element 153 in the channel direction may form the center channel Ch2N.

The shift amount (distance dN) of the X-ray detection elements in the normal mode is equal to ¼ of a channel width in the normal mode (that is, a total width of two X-ray detection elements in the aforementioned example). For example, if a single X-ray detection element has a width of 1 mm, the distance dN is expressed as "dN=2 mm×¼=0.5 mm".

Herein, the distance dH shown in FIG. 5 and the distance dN shown in FIG. 6 have a magnitude relationship represented by equation (1) below.

$$dH < dN \quad (1)$$

As described above, the position of the channel's center is shifted in the channel direction between the high-resolution mode and the normal mode. For example, assume that the X-ray detection elements 151-154 are arranged in positions shifted by ¼ of a channel in order to realize a ¼-offset arrangement in the high-resolution mode. In this high-resolution mode, the ¼-offset arrangement is realized even in terms of a channel unit because a channel is set to each X-ray detection element. Under this condition, if the high-resolution mode is later switched to the normal mode, a position on the center element, through which the X-ray path passes, remains unchanged because positions of the X-ray detection elements 151-154 are fixed. Therefore, if the high-resolution mode is later switched to the normal mode, the ¼-offset arrangement is not achieved in terms of a channel unit, and each of the channels is shifted by only ⅛ of a channel.

In order to realize offset arrangement based on a channel regardless of switching of the detector resolution modes, the X-ray CT apparatus according to the present embodiment moves the position of the X-ray path with respect to a channel's center according to a selected mode. In order to move the position of the X-ray path with respect to a channel's center, the X-ray CT apparatus according to the present embodiment adjusts a focal position on the anode 133 that the thermoelectrons collide with, by controlling a grid voltage to apply to the grid 137, for example.

Next, operation of the X-ray CT apparatus according to the present embodiment will be described with reference to FIGS. 7-11. Herein, the X-ray CT apparatus is based on the premise that a detector resolution mode set as a default is the high-resolution mode. Based on this premise, the plurality of X-ray detection elements are arranged in positions shifted in the channel direction by ¼ of a channel width according to the high-resolution mode, that is, by ¼ of a width of one X-ray detection element.

(Operation of X-Ray CT Apparatus with Normal Mode being Selected)

FIG. 7 is a flowchart showing the operation when a detector resolution mode is switched from the high-resolution mode to the normal mode within the X-ray CT apparatus according to the present embodiment.

First, the display 103 displays a selection window to select a mode. An operator makes selection operation through the input circuitry 105 to select the normal mode or the high-resolution mode. FIG. 7 assumes that the normal mode is selected by an operator through the input circuitry 105.

In step Sa1, the computing circuitry 101 determines whether a selection operation to select the normal mode is received from an operator through the input circuitry 105. In step Sa2, upon receipt of the selection operation to select the normal mode, the computing circuitry 101 switches a detector resolution mode from the high-resolution mode to the normal mode.

In step Sa3, the computing circuitry 101 instructs the gantry control circuitry 25 to control a grid voltage to apply to the grid. As instructed by the computing circuitry 101, the gantry control circuitry 25 controls a grid voltage through the grid control circuitry 45 in a manner so that thermoelectrons collide with a focal position on the anode 133, which corresponds to the selected normal mode. Specifically, the grid control circuitry 45 stores in memory, etc., a bias voltage value corresponding to a focal position according to the normal mode. As instructed by the gantry control circuitry 25, the grid control circuitry 45 reads from a memory, etc., a bias voltage value corresponding to a focal position according to the selected normal mode. The grid control circuitry 45 applies to the grid 137, a voltage corresponding to the read bias voltage value. By applying a voltage corresponding to the read bias voltage value to the grid 137, a focal position on the anode 133, that the thermoelectrons collide with, is shifted in the X-axis direction substantially parallel to the channel direction.

FIG. 8 is a view showing focal position FH according to the high-resolution mode and focal position FN according to the normal mode. FIGS. 9A and 9B are views each showing a positional relationship of an X-ray path with respect to X-ray detection elements and channels in the case of switching the high-resolution mode to the normal mode. As shown in FIG. 8, by a voltage corresponding to the read bias voltage value being applied to the grid 137, the gantry control circuitry 25 changes a focal position on the anode 133 that the thermoelectrons collide with, from the focal position FH according to the high-resolution mode to the focal position FN according to the normal mode.

This enables the gantry control circuitry 25 to collide thermoelectrons emitted from the cathode 131 with the focal position FN on the anode 133, which corresponds to the selected normal mode, as shown in FIG. 8. As shown in FIG. 9A, in the high-resolution mode, the channels Ch1H-Ch5H are set to the X-ray detection elements 151-155, respectively. In the high-resolution mode, the X-ray path IHs corresponding to the focal position FH passes through the position PHs which is shifted by ¼ of a channel from the channel's center PCH to one end of the center element 153. As shown in FIG. 9B, when the high-resolution mode is switched to the normal mode, channels are switched to the channels Ch1N-Ch3N for the normal mode. For example, the X-ray detection element 153 positioned in the channel's center and the X-ray detection element 154 positioned after the X-ray detection element 153 in the channel direction form the center channel Ch2N. If no change is made to an X-ray path, this X-ray path passes through a position which is shifted by ⅛ of a channel from one end of the center channel Ch2N.

When a focal position is changed from the position FH to the position FN along with the change from the high-resolution mode to the normal mode, as shown in FIG. 9B, the X-ray path INs corresponding to the focal position FN passes through the center PCH of the center element 153 (in other words, the position PNs that is shifted by ¼ of a channel from the center PCN to one end of the channel Ch2N in the normal mode). In other words, the position PNs corresponds to a position that is shifted by ⅛ of a width in the channel direction of the channel Ch2N from the position PHs through which the X-ray path passes in the high-resolution mode, to the channel's center PCN in the normal mode. Along with the change from the high-resolution mode to the normal mode, the X-ray path is shifted by ⅛ of a width in the channel direction of the channel Ch2N from the position PHs through which the X-ray path passes in the high-resolution mode, to the channel's center PCN in the normal mode.

Hereinafter, how to calculate a motion distance of a focal point in the case of changing a focal position from the focal position FH to the focal position FN will be described by giving a specific example. FIG. 10 is a view showing an example of how to calculate a motion distance of a focal point shown in FIG. 8. As shown in FIG. 10, assume that distances are set as follows. A distance between the focal position FH and the focal position FN is set to "a". A distance between the focal position FH and the center axis Z is set to "b". A distance between the position PH on the X-ray detection element, through which the X-ray path from the focal position FH passes, and the position PN on the X-ray detection element, through which the X-ray path from the focal position FN passes is set to "c". A distance between the position PN and the center axis Z is set to "d". According to this assumption, if the triangle FH-FN-Z and the triangle PH-PN-Z are similar in shape, equation (2) below is satisfied.

$$a:b=c:d \qquad (2)$$

The gantry control circuitry 25 calculates the focal point motion distance using the above equation (2). Herein, the focal point motion distance is calculated by using specific numeric values. The present embodiment assumes that each X-ray detection element has a width of 1 mm. The present embodiment assumes that incident position PH is shifted in advance by 0.25 mm in the channel direction because the X-ray detection elements are arranged in advance in positions shifted by ¼ of a channel in the channel direction in accordance to the high-resolution mode. Furthermore, The present embodiment assumes that the distance "b" is 450 mm and the distance "d" is 550 mm.

With the use of the equation (2), the distance "a" is determined as "a=b×c/d=450 mm×0.25 mm/550=0.204 . . . =0.20 mm". At this time, the distance "c" is determined as follows: "the shift amount (distance dN) of X-ray detection elements shifted by ¼ of a channel under the normal mode—the shift amount (distance dH) of X-ray detection elements shifted in advance in the channel direction" That is, the position of the X-ray path can be shifted by 0.25 mm in the channel direction by shifting a focal position on the anode 133 that the thermoelectrons collide with, by 0.20 mm in the X-axis direction. That is, the X-ray path can be set in a position shifted by ¼ of a channel in the channel direction under the normal mode. Accordingly, a channel-based ¼-offset arrangement can be realized in the normal mode.

The above-described embodiment is based on the premise that the X-ray detection element 153 positioned in the channel's center and the X-ray detection element 154 positioned after the X-ray detection element 153 in the channel direction form the channel Ch2N for the normal mode. However, the present embodiment is not limited to this premise. That is, the X-ray detection element 153 positioned in the channel's center and the X-ray detection element 152 positioned before the X-ray detection element 153 in the channel direction may form the channel Ch2N for the normal mode. With the channels configured as described above, when a focal position is changed from the position FH to the position FN along with the change from the high-resolution mode to the normal mode, as shown in FIGS. 11A and 11B, the X-ray path INs corresponding to the focal position FN passes through the center PCH of the center element 153. That is, the X-ray path INs passes through the position PNs shifted by ⅛ of a channel from the center PCN to one end (to be more specific, one of both ends, which is closer to the position PHs) of the channel Ch2N in the normal mode. Along with the change from the high-resolution mode to the normal mode, the X-ray path is shifted by ⅛ of a width in the channel direction of the channel Ch2N from the position PHs through which the X-ray path passes in the high-resolution mode, to the opposite side of the channel's center PCN in the normal mode.

Figure 12A:
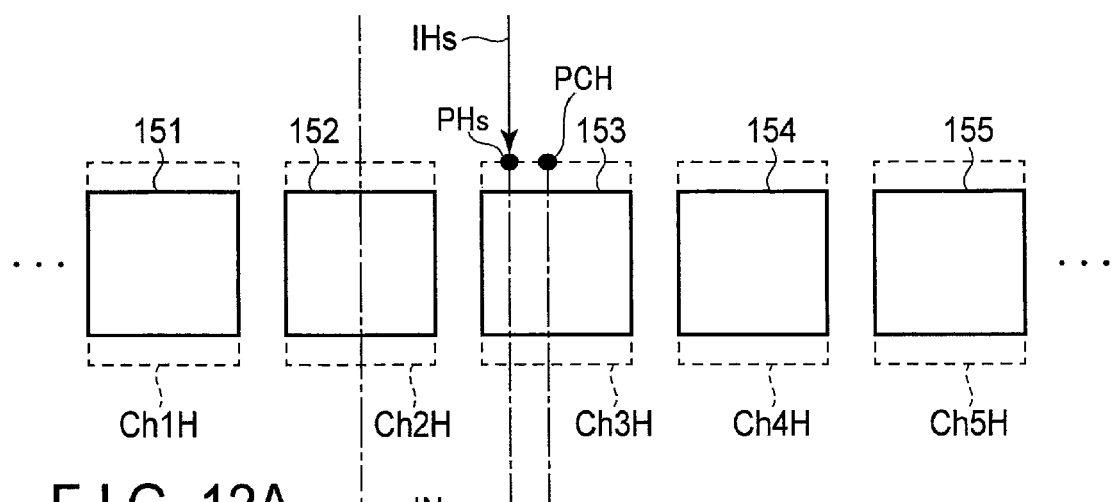
FIGS. 12A and 12B are views each showing yet another positional relationship of an X-ray path with respect to X-ray detection elements and channels in the case of switching from the high-resolution mode to the normal mode.
Figure 12B:
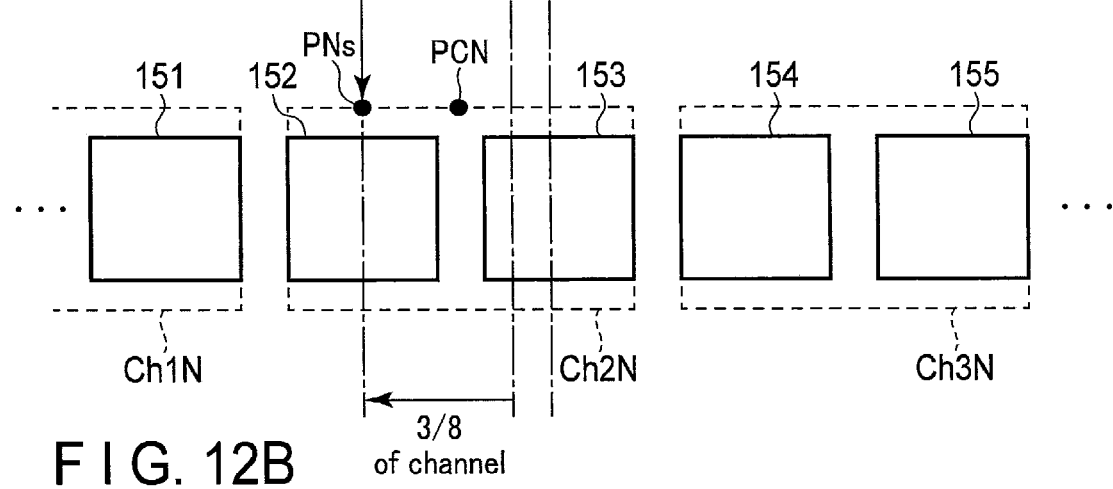

As shown in FIGS. 12A and 12B, the X-ray path INs corresponding to the focal position FN may pass through the position PNs shifted by ⅜ of a channel from the center PCN of the channel Ch2N in the normal mode, to one of both ends, which is further away from the position PHs. In such a case, along with the change from the high-resolution mode to the normal mode, the X-ray path is shifted by ⅜ of a width in the channel direction of the channel Ch2N from the position PHs through which the X-ray path passes in the high-resolution mode, in the direction to the channel's center PCN in the normal mode.

(Operation of X-Ray CT Apparatus with High-Resolution Mode being Selected after Selection of Normal Mode)

Figure 13:
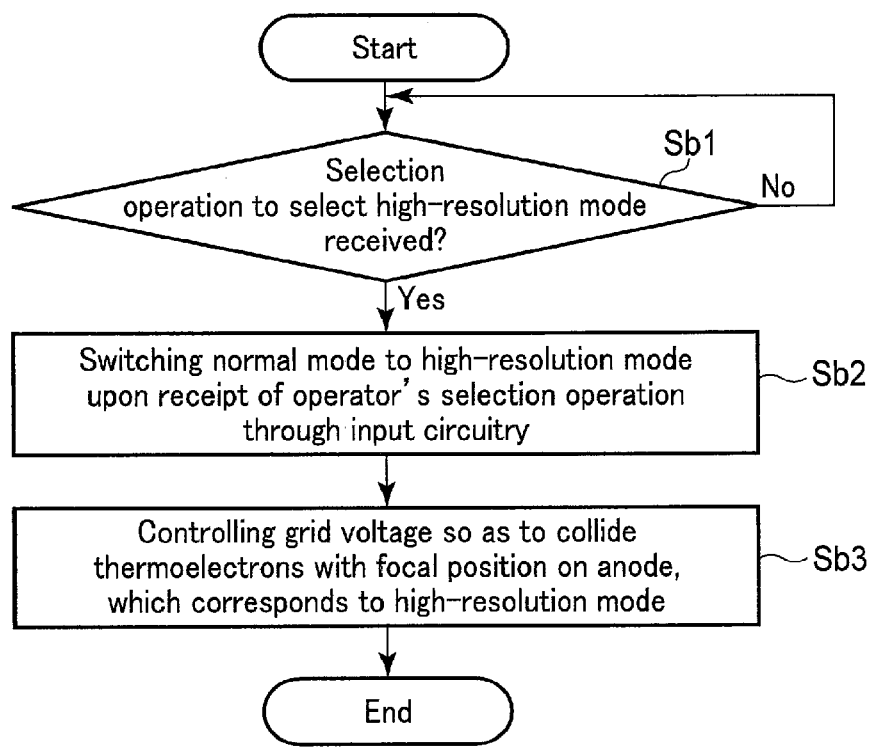
FIG. 13 is a flowchart showing how the X-ray CT apparatus according to the present embodiment operates in the case of switching from the normal mode to the high-resolution mode.

FIG. 13 is a flowchart of operation within the X-ray CT apparatus according to the present embodiment when a detector resolution mode is switched from the normal mode to the high-resolution mode.

First, the display 103 displays a selection window to select a detector resolution mode. An operator makes selection operation through the input circuitry 105 to select the normal mode or the high-resolution mode. Herein, assume that the high-resolution mode is selected by an operator through the input circuitry 105.

In step Sb1, the computing circuitry 101 determines whether a selection operation to select the high-resolution mode is received from an operator through the input circuitry 105. In step Sb2, upon receipt of the selection operation to select the high-resolution mode, the computing circuitry 101 switches a detector resolution mode from the normal mode to the high-resolution mode.

In step Sb3, the computing circuitry 101 instructs the gantry control circuitry 25 to control a grid voltage to apply to the grid. As instructed by the computing circuitry 101, the gantry control circuitry 25 controls a grid voltage through the grid control circuitry 45 in a manner so that thermoelectrons collide with a focal position on the anode 133, which corresponds to the selected high-resolution mode. Specifically, the grid control circuitry 45 stores in a memory, etc., a bias voltage value corresponding to a focal position according to the high-resolution mode. As instructed by the gantry control circuitry 25, the grid control circuitry 45 reads from a memory, etc., a bias voltage value corresponding to a focal position according to the selected high-resolution mode. The grid control circuitry 45 applies to the grid 137, a voltage corresponding to the read bias voltage value. By applying a voltage corresponding to the read bias voltage value to the grid 137, a focal position on the anode 133, with which thermoelectrons collide, is shifted in the X-axis direction substantially parallel to the channel direction.

Figure 14:
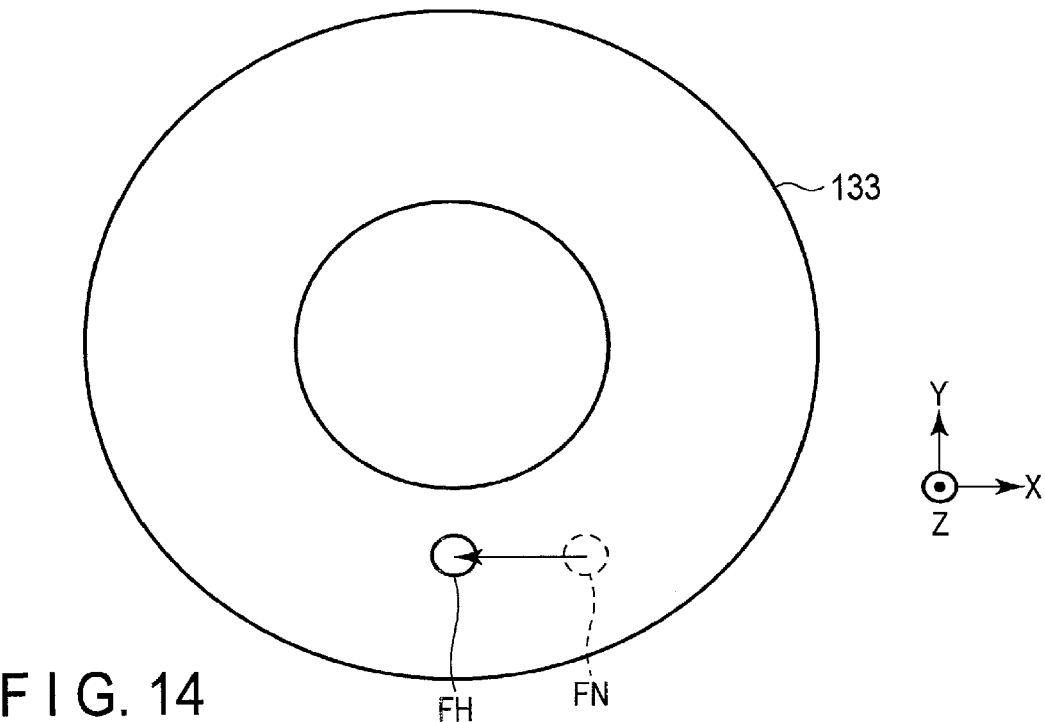
FIG. 14 is a view showing a focal position according to the high-resolution mode according to FIG. 13 and a focal position according to the normal mode.

FIG. 14 is a view showing the focal position FH according to the high-resolution mode and the focal position FN according to the normal mode. As shown in FIG. 14, by applying a voltage corresponding to the read bias voltage value to the grid 137, the X-ray CT apparatus according to the present embodiment changes a focal position on the anode 133 that the thermoelectrons collide with, from the focal position FN according to the normal mode to the focal position FH according to the high-resolution mode.

This enables the X-ray CT apparatus according to the present embodiment to collide thermoelectrons emitted from the cathode 131 with the focal position FH on the anode 133 according to the selected high-resolution mode, as shown in FIG. 14.

With the above configuration, the X-ray CT apparatus according to the embodiment controls a focal position on the anode 133 that the thermoelectrons collide with by controlling a grid voltage to apply to the grid 137. In this manner, the X-ray CT apparatus according to the embodiment control can shift the position of the X-ray path. That is, the X-ray CT apparatus according to the present embodiment achieves a channel-based ¼-offset arrangement regardless of whether a mode is the normal mode or the high-resolution mode.

The above embodiment described how the X-ray CT apparatus operates when the normal mode is selected and how the X-ray CT apparatus operates when the high-resolution mode is selected after selection of the normal mode. On the other hand, there is a case where the high-resolution mode is selected by an operator through the input circuitry 105. However, the plurality of X-ray detection elements are arranged in advance in positions shifted by ¼ of a channel in the channel direction in accordance with the high-resolution mode. This eliminates the need for the X-ray CT apparatus according to the present embodiment to adjust the position of the X-ray path even if an operator selects the high-resolution mode through the input circuitry 105.

As described above, the X-ray CT apparatus according to the present embodiment includes the X-ray tube 13, the X-ray detector 15, and the gantry control circuitry 25. The X-ray tube 13 generates X-rays. The X-ray detector 15 includes the plurality of X-ray detection elements that detect X-rays generated by the X-ray tube 13. The gantry control circuitry 25 adjusts the position of the X-ray path with respect to the plurality of X-ray detection elements based on the normal mode or the high-resolution mode.

With the above configuration, even if the plurality of the X-ray detection elements are arranged in positions shifted by a predetermined distance in the channel direction in accordance with one of the normal mode and the high-resolution mode, the X-ray CT apparatus according to the present embodiment can adjust the position of the X-ray path according to the other mode by adjusting the position of the X-ray path with respect to the respective X-ray detection elements.

In this manner, the X-ray CT apparatus according to the present embodiment achieves a channel-based ¼-offset arrangement regardless of switching of the detector resolution modes.

Described in the above embodiment is the configuration in which the position of the X-ray path is moved by adjusting a focal position on the anode 133, that the thermoelectrons collide with. However, the X-ray CT apparatus according to the present embodiment is not limited to this configuration. For example, the X-ray CT apparatus according to the present embodiment may include at least one of an X-ray tube moving mechanism for making the X-ray tube 13 movable in the center axis Z of rotation, and a detector moving mechanism for making the X-ray detector 15 movable in the channel direction. The X-ray CT apparatus may move the position of the X-ray path by the X-ray moving mechanism's moving the X-ray tube 13 along the center axis Z of rotation. The X-ray CT apparatus may move the position of the X-ray path by the detector moving mechanism's moving the X-ray detector 15 in the channel direction. At this time, the gantry control circuitry 25 may control the amount of movement of the X-ray tube 13 by the X-ray moving mechanism. The gantry control circuitry 25 may control the amount of movement of the X-ray detector 15 in the channel direction by the detector moving mechanism.

Described in the above embodiment is the configuration in which each of the X-ray detection elements is arranged in advance in a position shifted by ¼ of a channel in the channel direction. However, the X-ray CT apparatus according to the present embodiment is not limited to this configuration. The X-ray CT apparatus according to the present embodiment is adaptable to the case where the X-ray detection elements are arranged in a normal manner without shifting each of the X-ray detection elements in advance by ¼ of a channel in the channel direction. In the case where the high-resolution mode is selected, the X-ray CT apparatus according to the present embodiment may control a grid voltage to apply to the grid 137 in a manner to collide thermoelectrons emitted from the cathode 131 to the focal position FH on the anode 133 according to the selected high-resolution mode. In the case where the normal mode is selected, the X-ray CT apparatus according to the present embodiment may control a grid voltage to apply to the grid 137 in a manner to collide thermoelectrons emitted from the cathode 131 to the focal position FN on the anode 133 according to the selected normal mode.

The term "processor" used in the above explanation means, for example, an exclusive or general processor, a circuit (circuitry), a processing circuit (circuitry), an operation circuit (circuitry), an arithmetic circuit (circuitry), or a circuit such as an Application Specific Integrated Circuit (ASIC) or a programmable logic device (for example, a Simple Programmable Logic Device (SPLD), a Complex Programmable Logic Device (CPLD), or a Field Programmable Gate Array (FPGA)). In addition, each component (each processing unit) according to the present embodiment may be implemented by not only a single processor, but also a plurality of processors. Furthermore, a plurality of components (a plurality of processing units) may be implemented by a single processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
an X-ray tube that generates X-rays;
an X-ray detector that includes a plurality of X-ray detection elements that detect X-rays generated by the X-ray tube; and
control circuitry that adjusts a position of an X-ray path with respect to the X-ray detection elements based on selection of a first mode for generating an image having a first resolution corresponding to a first bundle unit of at least one of the X-ray detection elements, or selection of a second mode for generating an image having a second resolution lower than the first resolution and corresponding to a second bundle unit of at least one of the X-ray detection elements different from the first bundle unit.

2. The X-ray computed tomography apparatus according to claim 1, wherein the control circuitry moves the X-ray path to a position shifted by ¼ of a channel in a channel direction with respect to a center of the channel.

3. The X-ray computed tomography apparatus according to claim 1, wherein the control circuitry adjusts the position of the X-ray path by adjusting a focal position in the X-ray detector.

4. The X-ray computed tomography apparatus according to claim 3, wherein each of the X-ray detection elements is set to a different channel in the first mode, and the control circuitry adjusts the focal position in a manner so that the X-ray path is set in a position shifted by ¼ of a channel in a channel direction with reference to a center of the channel.

5. The X-ray computed tomography apparatus according to claim 4, wherein the X-ray detector causes the X-ray detection elements to output detection signals of the X-rays with each of the X-ray detection elements being set to a different single channel in the first mode.

6. The X-ray computed tomography apparatus according to claim 3, wherein a predetermined number of adjacent X-ray detection elements of the X-ray detection elements are set to a single channel in the second mode, and the control circuitry adjusts the focal position in a manner so that the X-ray path is set in a position shifted by ¼ of a channel in a channel direction with reference to a center of the channel.

7. The X-ray computed tomography apparatus according to claim 6, wherein the X-ray detector causes the X-ray detection elements to output detection signals of the X-rays in the second mode with the predetermined number of adjacent X-ray detection elements being set to a single channel.

8. The X-ray computed tomography apparatus according to claim 3, which calculates a shift amount of the focal position based on:
- a distance between a focal position according to the first mode and a center axis around which the X-ray tube and the X-ray detector are rotated;
- a distance between a position on the X-ray detector in which X-rays generated from a focal position according to the first mode enter, and a position on the X-ray detector in which X-rays generated from a focal position according to the second mode enter; and
- a distance between the center axis and the position on the X-ray detector in which X-rays generated from the focal position according to the first mode enter.

9. The X-ray computed tomography apparatus according to claim 1, wherein the X-ray detection elements are arranged in positions shifted by ¼ of a channel in a channel direction with respect to a center of the channel.

10. The X-ray computed tomography apparatus according to claim 1, wherein
- the X-ray detection elements include a first X-ray detection element and a second X-ray detection element positioned after the first X-ray detection element in a channel direction,
- the first X-ray detection element and the second X-ray detection element are set to a single channel in the second mode, and
- the control circuitry shifts the X-ray path by ⅛ of a channel to a center of the channel at a time of switching from the first mode to the second mode.

11. The X-ray computed tomography apparatus according to claim 1, wherein
- the X-ray detection elements include a first X-ray detection element and a third X-ray detection element positioned before the first X-ray detection element in a channel direction,
- the first X-ray detection element and the third X-ray detection element are set to a single channel in the second mode, and
- the control circuitry shifts the X-ray path by ⅜ of a channel to a center of the channel or by ⅛ of the channel to an opposite side of the center of the channel at a time of switching from the first mode to the second mode.

12. The X-ray computed tomography apparatus according to claim 1, further comprising input circuitry that receives a selection operation to select the first mode or the second mode, wherein the control circuitry adjusts the position of the X-ray path with respect to the X-ray detection elements upon receipt of the selection operation through the input circuitry.

13. The X-ray computed tomography apparatus according to claim 1, wherein the control circuitry controls an X-ray high voltage device that moves a position of a focal point formed in an anode of the X-ray tube in order to adjust the position of the X-ray path.

14. The X-ray computed tomography apparatus according to claim 1, wherein the control circuitry controls at least one of an X-ray tube moving mechanism for making the X-ray tube movable along a center axis of rotation, and an X-ray detector moving mechanism for making the X-ray detector movable in a channel direction in order to adjust the position of the X-ray path.

* * * * *